United States Patent [19]

Baeumle et al.

[11] Patent Number: 4,737,150
[45] Date of Patent: Apr. 12, 1988

[54] TWO-CANNULA SYRINGE

[75] Inventors: Hubert Baeumle, Escholzmatt; Eckard Schwoebel, Lucerne, both of Switzerland

[73] Assignee: Intermedicat GmbH, Emmenbrucke, Switzerland

[21] Appl. No.: 858,365

[22] Filed: Apr. 30, 1986

[30] Foreign Application Priority Data

May 10, 1985 [EP] European Pat. Off. ........ 85105748.9

[51] Int. Cl.$^4$ .............................................. A61M 5/32
[52] U.S. Cl. .................................... 604/198; 604/239; 604/411
[58] Field of Search ........................ 604/51, 158–169, 604/192–198, 239, 272–274, 411–414, 905; 141/329, 330

[56] References Cited

U.S. PATENT DOCUMENTS

| 2,626,603 | 1/1953 | Gabriel | 604/414 |
| 2,630,803 | 3/1953 | Baran | 604/158 |
| 3,008,570 | 11/1961 | Roehr et al. | 604/197 X |
| 3,292,624 | 12/1966 | Gabriel et al. | 604/192 |
| 3,940,003 | 2/1976 | Larson | 604/411 |
| 4,059,112 | 11/1977 | Tischlinger | 604/413 |
| 4,518,383 | 5/1985 | Evans | 604/51 |

Primary Examiner—Dalton L. Truluck
Attorney, Agent, or Firm—Ladas & Parry

[57] ABSTRACT

A two-cannula syringe for the aspiration and for the injection of medicaments in the form of liquids. The syringe includes a first cannula for the aspiration of the liquid into a cylinder of the syringe and for the possible mixing and/or degassing of the liquid and a second cannula for the actual injection. Both cannulae are present in a protected state, the first cannula being disposed so as to be displaced relative to the second and/or so as to be removable or displaceable in the longitudinal direction of the syringe, and both cannulae being disposed about the same longitudinal axis of the syringe.

6 Claims, 4 Drawing Sheets

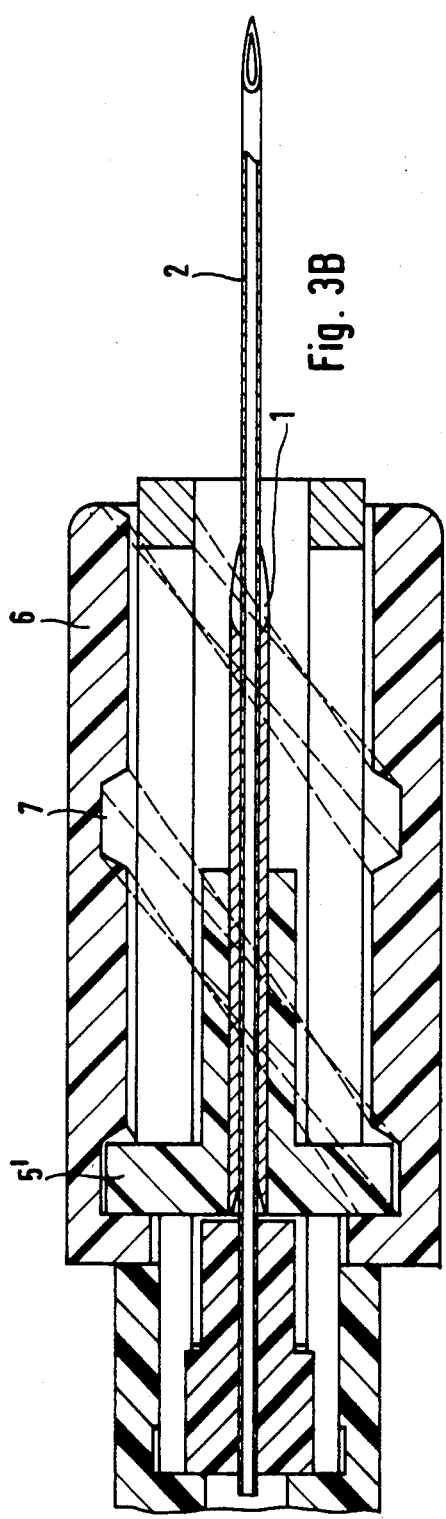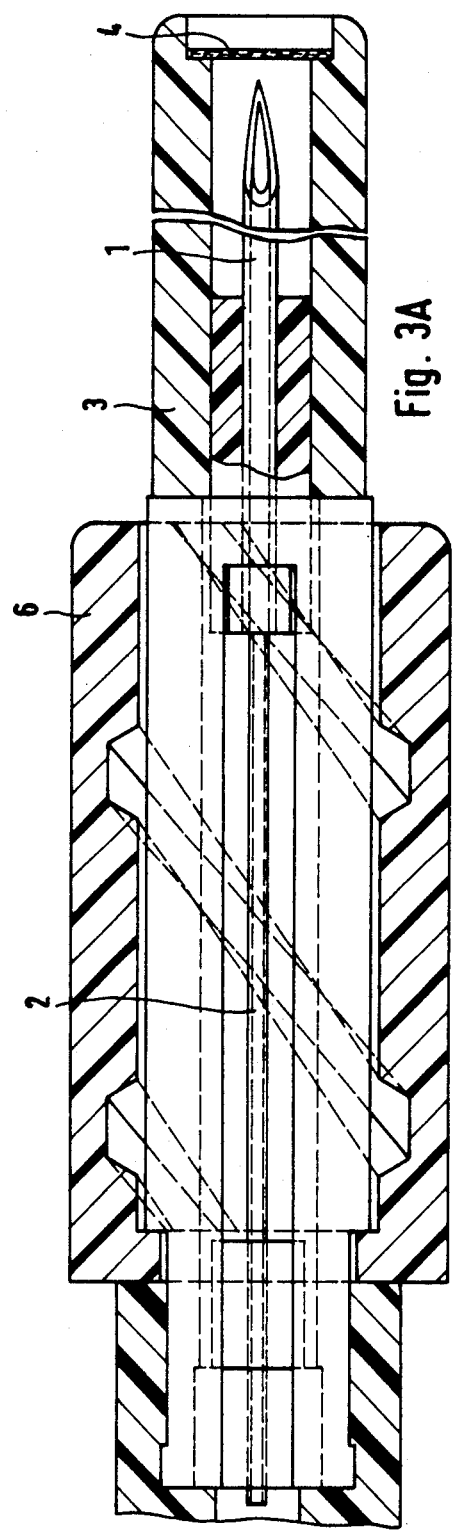

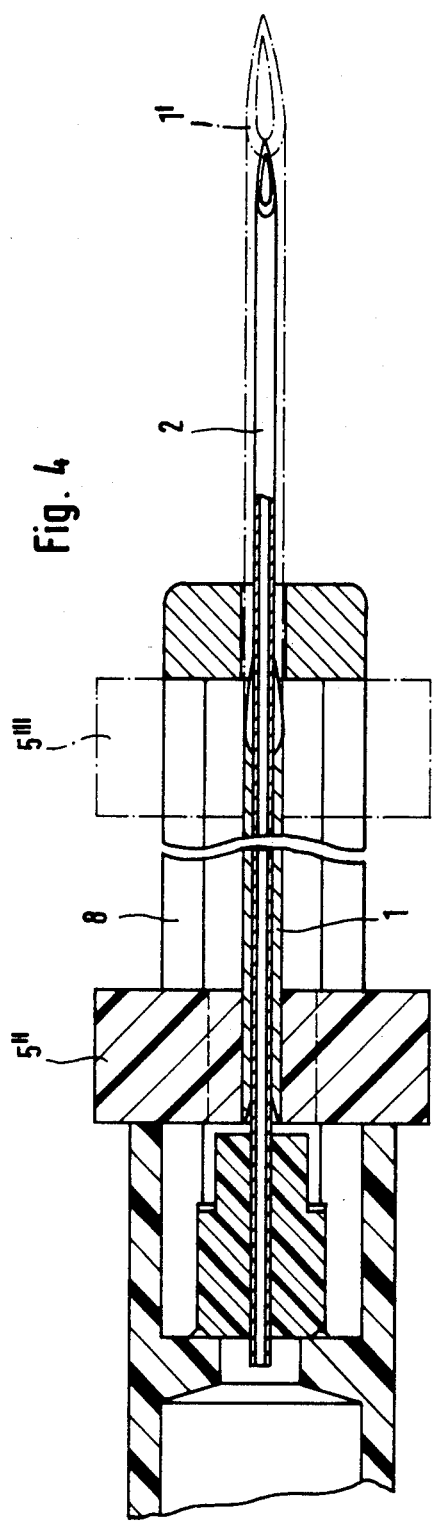

TWO-CANNULA SYRINGE

BACKGROUND OF THE INVENTION

The present invention relates to a two-cannula syringe for the aspiration and injection of medicaments in the form of liquids.

Hypodermic syringes with a removable and thus also exchangeable cannula are known, inter alia from Swiss Pat. Nos. 590,661 and 639,856 as well as from European Patent Application, Publication No. 0,047,442.

Syringes for the self-injection of insulin solutions are described, inter alia, in European Patent Application, Publication No. 0,045,367. Reference is indeed generally made, in this European patent application, to the risks of contamination which arise in such applications (page 3), but there is no specific reference to the fact that it is the cannula which—above all in the case of repeated use—shows the greatest probability of contamination and thus represents the greatest risk of infection.

Working with throw-away hypodermic syringes also brings only an inadequate reduction of the risk of contamination: it is the place of puncturing, used over a relatively long period of time, of the medicine phial which primarily enters into consideration in connection with the transfer of germs to the cannula.

Even the exchange of the cannula between aspiration and injection can indeed lead to contamination, above all when the solution remains uncovered in the syringe during exchange or when such exchange requires contact with the cannula.

A double-cannula extraction device for sterile applications is described and claimed in European Patent Application, Publication No. 0,085,957. A puncturable double-cannula is represented specifically in the devices according to FIGS. 5 and 9 of this application, in which devices the two cannulae are designed to be located adjacent to one another and are also inserted together into the solution container. Through one of the cannulae liquid is extracted, and through the other air is introduced into the container under sterile conditions, for the purpose of pressure compensation.

Operating with one cannula for aspiration or filling and for injection does, moreover, conceal the danger of damage of the cannula, which can have a negative effect in the course of injection.

West German Pat. No. 378,629 teaches and claims a medicinal syringe, over the cannula of which—after introduction of the same into the blood vessel—a protective tube with blunt edges and without a tip can be pressed, in order in this manner to protect the interior of the blood vessel from the tip of the cannula. By definition, the protective tube cannot be used as an extraction or aspiration tube for liquid medicaments.

Finally, in German Utility Model No. 1,678,482, a small protective tube is described, which in the course of filling the syringe, for the purpose of the mechanical protection of the injection cannula, is placed on the latter. As is clearly evident, the small protective tube is conceived for a multiplicity of syringes; this clearly contradicts the most important aim of the two-cannula syringe of the invention, namely the minimization of contamination. In addition to this, before the syringe is used it is uncovered.

Only by means of the two-cannula syringe according to the invention described here, however, is the problem of exchange-free changing of cannulae between aspiration and injection fundamentally recognized and solved.

SUMMARY OF THE INVENTION

According to the invention, a two-cannula syringe for the aspiration and for the injection of medicaments in the form of liquids is provided, which is characterized in that the syringe exhibits a) a first cannula for the aspiration of the liquid onto the cylinder of the syringe and for the possible mixing and/or degassing of the liquid, and b) a second cannula for the actual injection, both cannulae being present in a protected state, the first cannula being disposed so as to be displaced relative to the second and/or so as to be removable or displaceable in the longitudinal direction of the syringe, and both cannulae being disposed about the same longitudinal axis of the syringe.

In applicant's first embodiment, there is shown a two-cannula syringe designed in such a manner that the first cannula is disposed to be removable in front of the second cannula, a protective cap with a filter to the environment being disposed about the first cannula, and the mounting of the said first cannula forming the protective cap of the said second cannula, and the second cannula projecting into the first cannula during the storage and aspiration phases.

In applicant's second embodiment there is shown a two-cannula syringe in such a manner that the first cannula is disposed to be removable in front of the second cannula, a protective cap being disposed about the first cannula, and the mounting of the said first cannula forming the protective cap of the said second cannula with inclusion of an intermediate filter, and the second cannula being disposed behind the first cannula and not projecting into the latter during the storage and aspiration phase.

In applicant's third embodiment a syringe is shown designed in such a manner that the first cannula is secured in a mounting movable relative to the syringe, which mounting is movable forwards and backwards in the longitudinal direction by rotation of the external guide ring about the screw thread, whereby the first cannula is displaced in front of or behind the tip of the second cannula, the first and second cannulae being situated in a protective cap with a filter to the environment during the storage phase. Finally, a last group of two-cannula syringes according to the invention is designed in such a manner that the first cannula is secured in a mounting movable relative to the syringe, which mounting is movable forwards and backwards in the longitudinal direction by sliding in a recess of the guide cylinder, whereby the first cannula is displaced in front of or behind the tip of the second cannula, the first and second cannulae being situated in a protective cap with a filter to the environment during the storage phase.

In the case of the last two groups of two-cannula syringes, there can be provided at the beginning and at the end of the range of movement of the mounting fixings for the latter.

DESCRIPTION OF THE DRAWINGS:

FIG. 3A—Is a sectional view of a third embodiment of the syringe of the present invention;

FIG. 3B—Is a further sectional view of the third embodiment of the syringe of the present invention showing the mounting means of the two-cannula;

FIG. 4—Is a sectional view of a fourth embodiment of the invention.

DETAILED DESCRIPTION OF THE INVENTION

BRIEF DESCRIPTION OF THE FIGURES

Figures 1A, 1B:
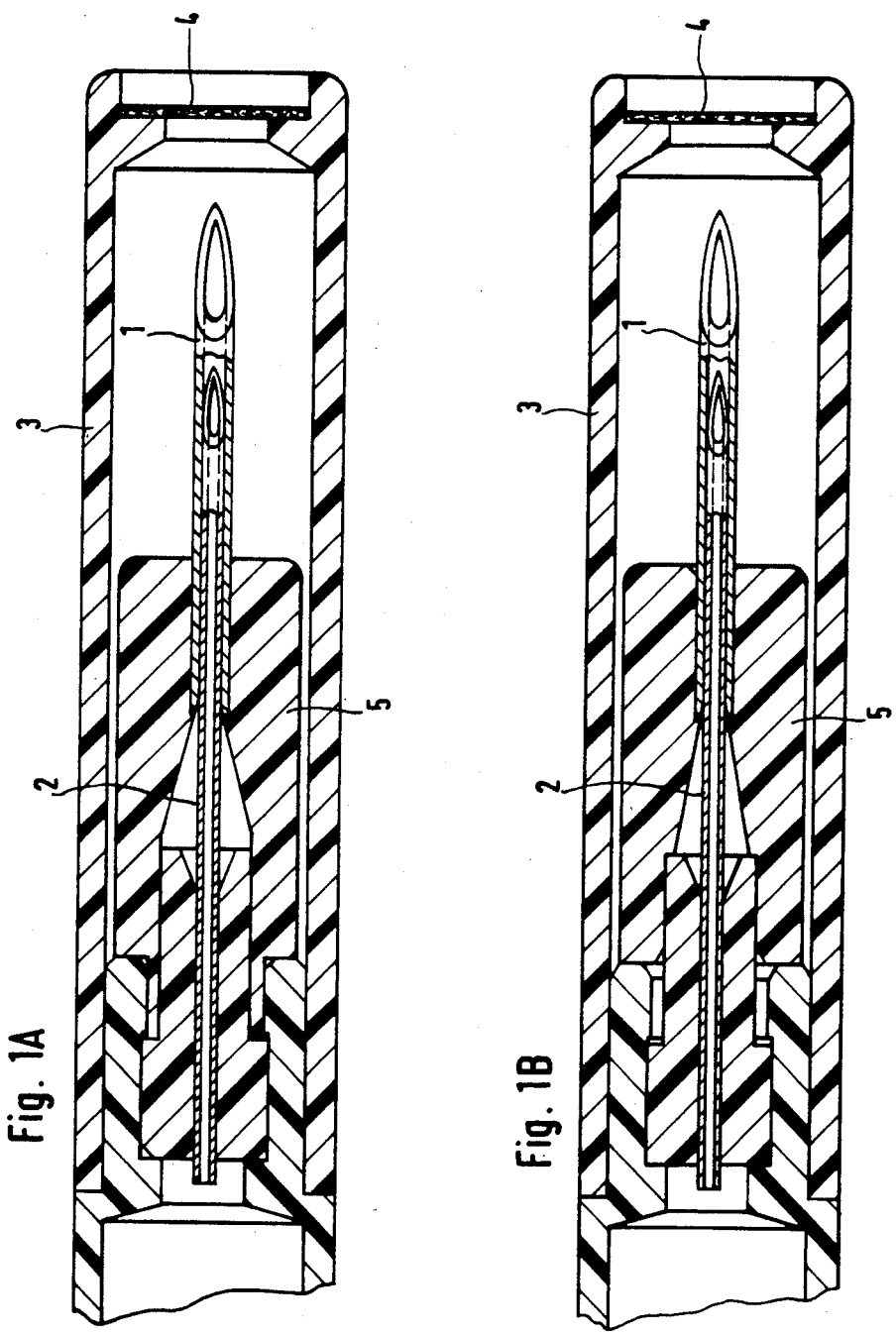
FIG. 1A—Is a sectional view of a first embodiment of the syringe of the present invention.
FIG. 1B—Is a further sectional view of the first embodiment of the syringe of the present invention.

The above described groups of embodiments of the two-cannula syringes according to the invention will be explained in greater detail hereinbelow with reference to the accompanying drawings in FIGS. 1 to 4; at the same time, the reference numerals which have already been used above will also be illustrated.

Figure 2:
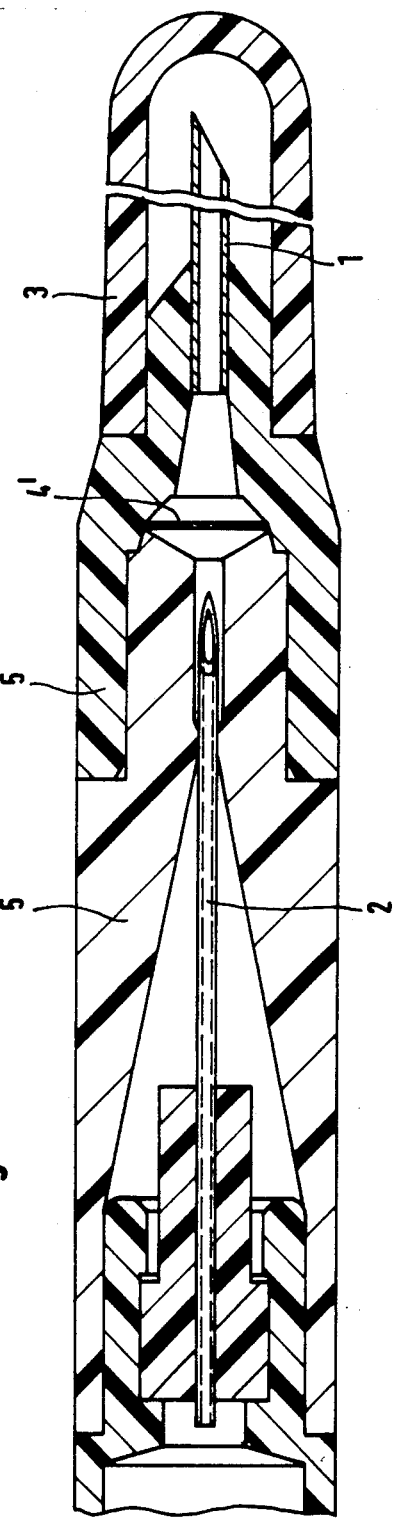
FIG. 2—Is a sectional view of a second embodiment of the syringe of the present invention.

FIGS. 1A and 1B depict two similar two-cannula syringes in cross-section;

FIG. 2 shows a modified two-cannula syringe in cross-section;

FIGS. 3A and 3B show two embodiments of a further modified two-cannula syringe in cross-section; and FIG. 4 depicts the two-cannula syringe of the embodiments shown in FIGS. 3A and 3B in various phases of operation.

DETAILED DESCRIPTION OF THE INVENTION

FIGS. 1A and 1B show the two-cannula syringes, according to the invention, of the above described first group, in the storage and transport phase. The second cannula 2 is situated within the first 1; both are accommodated in the cap 3 with a filter towards the outside 4. For aspiration, the protective cap is removed. After filling the cylinder of the syringe with the liquid, the first cannula together with the mounting 5 is removed. Only by this means does the second cannula become free for the actual injection.

FIG. 2 shows the two-cannula syringe, according to the invention, of the above described second group, likewise in the storage and transport phase. The first cannula 2 is situated separately in front of the second cannula 2. Around the first cannula there is situated the protective cap 3, which is removed for the purpose of aspiration. When the liquid is drawn in, it passes through the filter 4', which is produced from a material suitable for this purpose and is secured in the mounting 5 of the first cannula. After aspiration, the first cannula together with its mounting and together with the intermediate filter is removed; cannula 2 is free for the injection.

FIGS. 3B and 3B show the two-cannula syringes, according to the invention, of the above described further group, both in the storage or transport phase (3A) and in the injection phase (3B).

The following can be seen in FIG. 3A: the first cannula 1, the second cannula 2, the protective cap and the guide ring 6.

In FIG. 3A, it is possible to see not only the components just mentioned of the two-cannula syringes according to the invention but also the actual mounting 5' of the first cannula and the screw thread 7.

For the aspiration of liquid, the protective cap 3 is removed and the first cannula is brought into the position according to FIG. 3A, or left there. After the liquid has been drawn into the syringe, the first cannula 1 is brought into the position according to FIG. 3B by rotation of the guide ring 6; the syringe is ready for the injection.

Finally, FIG. 4 shows the two-cannula syringe, according to the invention, of the above described last group of embodiments according to the invention, without a protective cap, in various phases of application.

That is, in FIG. 4 there is shown a first cannula (1) secured to a mounting (5") movable relative to the syringe, which mounting (5") is movable between a forward and a backward position. The mounting (5") slides between these two positions in a recess defined in a guide cylinder (8). This sliding movement causes the first cannula (1) to be displaced in front of or behind the tip of a second cannula (2).

The above indicated filtration of the air is very important in the aspiration of the liquid medicament from a rigid container; the air flowing into the container must be filtered under sterile conditions. Such sterile filtration of the air can take place by means of adaptation readily evident to a person skilled in the art—of the air filters and of the second cannula of the syringe system according to the invention.

During aspiration, the first cannula together with the mounting is situated in the forward position 1', 5''', and subsequently, i.e. during injection, it is situated in the rear position 1, 5''. The guiding of the said mounting takes place by displacement of the same in one or more recesses in the guide cylinder 8.

The fact that, in the case of the two-cannula syringe according to the invention, the actual injection cannula is protected from damage during the storage and aspiration phases, should likewise be noted here.

The described two-cannula syringes are produced from suitable materials and, in particular, from plastic materials for the syringe body, cylinder piston rod and protective cap, metal or plastic material, especially steel for the cannula and synthetic or natural rubber for the piston.

The two-cannula syringes, according to the present invention, are employed for the aspiration and injection of medicaments in the form of liquids, without exchange of the cannula, for which purpose storage or transport phases, aspiration phases and injection phases are to be distinguished.

Specifically, the two-cannula syringes, according to the above and second embodiments, are employed in such a manner that during the storage or transport phase the first cannula is disposed in front of the second cannula, that both cannulae being protected by a protective cap. To use the syringe, the protective cap (3) is removed for the aspiration or mixing/degasing of the liquid, then the first cannula together with the complete mounting (5) is removed to expose the second cannula to use as an instrument for injection of the liquid.

The two-cannula syringes, according to the above third and fourth embodiments, are employed in such a manner that during the storage or transport phase, the second cannula and possibly the first cannula are protected by a protective cap, the protective cap (3) is removed for the aspiration or mixing/degasing of the liquid by the first cannula, the first cannula being brought into a position in front of the tip of the second cannula. Upon completion of aspiration, the first cannula is brought into the position behind the tip of the second cannula at which time the second cannula may be used to inject the liquids earlier aspirated.

The described four groups of two-cannula syringes according to the invention are to be regarded as indications by way of example; further embodiments are possible without further ado, on the basis of the concept of the invention.

We claim:

1. A syringe assembly comprising:
   (a) an injection cannula having two ends, one end being connected to said assembly the other end being a free end, said injection cannula being movable between a front position and a back position;
   (b) an aspiration cannula surrounding and slidably engaging said injection cannula, said aspiration cannula being operable to puncture containers containing sealed liquids and to aspirate, degas, and remix the liquids as they pass through said aspiration cannula into said injection cannula through said free end, said aspiration cannula extending beyond said free end when said injection cannula is in said back position, said free end extending outside of said aspiration cannula when said injection cannula is in said forward position; and
   (c) guiding means operably attached to said injection cannula for moving said injection cannula between said front and back positions, such that by upon placing said injection cannula in said back position, said aspiration cannula may be used to aspirate liquids into said syringe assembly without soiling said free end of said injection cannula and upon moving said guide means and said injection cannula to said front position, said free end is made available to inject the liquid free of said aspiration cannula.

2. The syringe assembly of claim 1 wherein said guiding means comprises a support member defining engagement threads on its outersurface and a guide ring correspondingly threaded on its innersurface such that by rotating said guide ring about said support member said injection cannula is moved to and from said back position and said front position.

3. The syringe assembly of claim 1 further including removable protective means, said protective means surrounding said aspiration cannula when said injection cannula is in said back position, said protective means being spaced from said aspiration cannula and serving to protect said aspiration cannula from breakage and exposure, said support means including a filter means opposite said free end, said protective means being removed to use said aspiration cannula and said injection cannula.

4. The syringe assembly of claim 1 wherein said guiding means comprising a guide cylinder and a sliding means, said guide cylinder sliding on said sliding means to move said cannula between said front and back positions.

5. The syringe assembly of claim 2 wherein said guiding means further comprises engagement means on said support member and said guide ring to lock said guide ring with respect to said support member in said front position and in said back position.

6. The syringe assembly of claim 4 wherein said guiding means further comprise engagement means on said guide cylinder and said sliding means to lock said injection cannula in said front position and said back position.

* * * * *